United States Patent
Lock et al.

(10) Patent No.: US 11,572,281 B2
(45) Date of Patent: Feb. 7, 2023

(54) METHOD FOR GRAPHENE FUNCTIONALIZATION THAT PRESERVES CHARACTERISTIC ELECTRONIC PROPERTIES SUCH AS THE QUANTUM HALL EFFECT AND ENABLES NANOPARTICLES DEPOSITION

(71) Applicant: The Government of the United States of America, as represented by the Secretary of the Navy, Arlington, VA (US)

(72) Inventors: Evgeniya H. Lock, Alexandria, VA (US); Michael S. Osofsky, Clarksville, MD (US); Raymond C Y Auyeung, Alexandria, VA (US); Rachael L. Myers-Ward, Springfield, VA (US); David Kurt Gaskill, Alexandria, VA (US); Joseph Prestigiacomo, Springfield, VA (US)

(73) Assignee: The Government of the United States of America, as represented by the Secretary of the Navy, Washington, DC (US)

(*) Notice: Subject to any disclaimer, the term of this patent is extended or adjusted under 35 U.S.C. 154(b) by 790 days.

(21) Appl. No.: 15/882,910

(22) Filed: Jan. 29, 2018

(65) Prior Publication Data
US 2018/0215623 A1 Aug. 2, 2018

Related U.S. Application Data

(60) Provisional application No. 62/453,324, filed on Feb. 1, 2017.

(51) Int. Cl.
*B32B 9/00* (2006.01)
*C01B 32/194* (2017.01)
(Continued)

(52) U.S. Cl.
CPC .......... *C01B 32/194* (2017.08); *G01N 33/50* (2013.01); *B82Y 15/00* (2013.01); *B82Y 30/00* (2013.01);
(Continued)

(58) Field of Classification Search
CPC ....... Y10T 428/30; B82Y 30/00; B82Y 40/00; C01B 32/194
(Continued)

(56) References Cited

U.S. PATENT DOCUMENTS

| | | | |
|---|---|---|---|
| 2012/0156424 A1 | 6/2012 | Chen et al. | |
| 2012/0202047 A1* | 8/2012 | Welch | B82Y 30/00 428/323 |

(Continued)

FOREIGN PATENT DOCUMENTS

WO 2011066332 A2 6/2011

OTHER PUBLICATIONS

Ciesielski, Artur, and Paolo Samori. "Graphene via sonication assisted liquid-phase exfoliation." Chemical Society Reviews 43.1 (2014): 381-398.
(Continued)

*Primary Examiner* — Daniel H Miller
(74) *Attorney, Agent, or Firm* — US Naval Research Laboratory; Rebecca L. Forman

(57) ABSTRACT

A method for graphene functionalization that preserves electronic properties and enables nanoparticles deposition comprising providing graphene, functionalizing the graphene via non-covalent or covalent functionalization, rinsing the graphene, drying the graphene, and forming functionalized graphene wherein the functionalized graphene preserves electronic properties and enables nanoparticles
(Continued)

Schematics of pyrene-based molecules

1 Hydroxypyrene

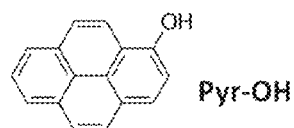

Pyr-OH

1 Pyrenecarboxylic acid

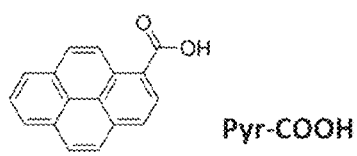

Pyr-COOH

Schematics of azide-based molecules

TFPA-NH$_2$ deposition. A functionalized graphene wherein the graphene functionalization preserves electronic properties and enables nanoparticles deposition.

12 Claims, 14 Drawing Sheets

(51) Int. Cl.
*G01N 33/50* (2006.01)
*B82Y 15/00* (2011.01)
*B82Y 30/00* (2011.01)
*B82Y 40/00* (2011.01)
*G01N 33/543* (2006.01)

(52) U.S. Cl.
CPC ........... *B82Y 40/00* (2013.01); *C01B 2204/22* (2013.01); *C01P 2002/82* (2013.01); *C01P 2006/32* (2013.01); *G01N 33/543* (2013.01); *Y10S 977/734* (2013.01); *Y10S 977/847* (2013.01); *Y10S 977/932* (2013.01); *Y10S 977/958* (2013.01)

(58) Field of Classification Search
USPC .......................................... 428/408; 423/448
See application file for complete search history.

(56) References Cited

U.S. PATENT DOCUMENTS

| | | | |
|---|---|---|---|
| 2012/0244358 A1* | 9/2012 | Lock | C01B 32/194 428/412 |
| 2014/0147938 A1* | 5/2014 | Imberty | C07H 15/26 436/501 |
| 2014/0193626 A1* | 7/2014 | Ozyilmaz | H01B 13/0033 428/220 |
| 2017/0321321 A1 | 11/2017 | Lock et al. | |
| 2017/0355902 A1* | 12/2017 | Moloney | F16L 58/1009 |
| 2017/0369322 A1* | 12/2017 | Mangadlao | B01J 23/52 |

OTHER PUBLICATIONS

Fu, Wangyang, et al. "High mobility graphene ion-sensitive field-effect transistors by noncovalent functionalization." Nanoscale 5.24 (2013): 12104-12110.

* cited by examiner

Schematics of pyrene-based molecules

1 Hydroxypyrene

Pyr-OH

1 Pyrenecarboxylic acid

Pyr-COOH

Schematics of azide-based molecules

TFPA-NH$_2$

METHOD FOR GRAPHENE FUNCTIONALIZATION THAT PRESERVES CHARACTERISTIC ELECTRONIC PROPERTIES SUCH AS THE QUANTUM HALL EFFECT AND ENABLES NANOPARTICLES DEPOSITION

REFERENCE TO RELATED APPLICATION

This application is a non-provisional of, and claims priority to and the benefits of, U.S. Provisional Patent Application No. 62/453,324 filed on Feb. 1, 2017, the entirety of which is hereby incorporated by reference.

BACKGROUND

This disclosure teaches a method to functionalize graphene to allow for modulation of graphene's electrical properties as well as for deposition of nanoparticles, such as oxides, metals, and quantum dots.

Graphene is a single layer of $sp^2$ bonded carbon, and has emerged as a unique conductor due to its zero-band gap, the ability to easily manipulate the carrier concentration and carrier type (electron or hole) through electrical gating, extremely high electron mobilities of 10 000-70 000 $cm^2V^{-1}s^{-1}$ and low absorption (2.3%) in the visible spectrum.

In addition, graphene is one of the strongest materials with a Young's modulus of 1 TPa and high thermal conductivity of 5000 $WmK^{-1}$. Furthermore, the quantum Hall effect was observed at room temperature.

However, graphene has an inert chemical nature so chemical functionalization is needed for integrating graphene with other materials, for the attachment of biomolecules and catalysts, and to allow the deposition of metals and dielectrics onto it. Both covalent and non-covalent approaches have been extensively explored.

It should be noted however that since graphene is all surface, any modification of its chemistry and structure leads to changes of its electrical properties as well so careful selection of the functionalization approach is needed.

The main covalent functionalization routes of graphene include free radical addition reactions, polymerization, cycloaddition, and introduction of single atoms (hydrogenation, fluorination, chlorination, oxygenation). Free radical reactions are based on the reduction of diazonium salts to form aryl radicals that attach to graphene forming $C(sp^3)$-aryl bonds and which can be achieved through thermal or electrochemical decomposition. This functionalization is very effective (12.7-20% coverage of nitrophenyl group was reported) but difficult to control and may also result in the formation of insulating layers on the graphene surface, thus hindering electronic device performance. Changes in the structure of graphene can be assessed using Raman spectroscopy—single layer graphene is characterized by two peaks at 1586 $cm^{-1}$ and 2686 $cm^{-1}$. If defects are present, then a D peak appears at 1350 $cm^{-1}$. The intensity ratio of D and G peaks is usually used as a measure of the degree of functionalization as well as an indication of the deterioration of the electrical properties. Reported values of $I_D/I_G$ in the case of aryl radical reactions varied—in one case 0.2-0.8, in another 2.6 for $SiC/EG-NO_2$-Ph. Cycloaddition reactions change the hybridization of pairs of neighboring atoms. Examples include the formation of cyclopropane or aziridine adducts, the formation of aryne or benzene intermediate via an elimination-addition mechanism, functionalization towards a five membered ring via six electrons cycloaddition between 1, 3 dipole and dipolarophile (graphene). The cycloaddition reactions latter provide a high level of control of the degree of functionalization and defect density, however it is reversible. Introduction of fluorine, chlorine and hydrogen atoms into the graphene lattice have been reported as well. However, that type of modification induced high levels of disorder—$I_D/I_G$=1.3-2.5 for Cl; $I_D/I_G$=1.0-1.5 for F; $I_D/I_G$=3.2 for H.

Non-covalent functionalization of graphene by graphene-ligand interactions is another approach.

An extensive literature review reveals that most of the work follows in two categories—attachment of molecules to graphene oxide (GO) followed by the reduction of the GO to graphene or using dispersed graphene nanopalets and functionalizing them in solution. There are only a few reports of functionalization of a complete graphene monolayer with ligands. Wang et. al. reported functionalization with pyrene butanoic acid sucidymidyel ester (PBSA) to change the power conversion of a solar cell from 0.21 to 1.71%. An et al. showed graphene functionalized with 1-pyrenecarboxylic acid (PCA) that was laminated onto PDMS membranes. The hybrid had unique optical properties—it blocked 70-95% of UV light and allowed more than 65% of the visible light. Pyrene functionalization of graphene was used for biosensing applications as well. Plasma-based functionalization of graphene is also possible; however, it greatly degrades the electronic properties of graphene (by increasing the resistivity).

The effect of the non-covalent pyrene- and pyridine based functionalization on graphene's electromagnetic properties has not been explored in the prior art and is one of the purposes of this invention.

The covalent azide based functionalization was realized in a way that does not damage graphene (no D peak) and is thus unique to this work. As a result, we observed the quantum Hall effect in functionalized graphene that is typical only for pristine graphene systems. This discovery will help in the development of quantum Hall resistance standards based on graphene technology and provides a platform for other graphene devices such as sensors with superior electronic properties compared to other functionalization methods.

SUMMARY OF DISCLOSURE

Description

This disclosure pertains to a method to functionalize graphene to allow for modulation of graphene's electrical properties as well as for deposition of nanoparticles, such as oxides, metals, and quantum dots.

DESCRIPTION OF THE DRAWINGS

The following description and drawings set forth certain illustrative implementations of the disclosure in detail, which are indicative of several exemplary ways in which the various principles of the disclosure may be carried out. The illustrated examples, however, are not exhaustive of the many possible embodiments of the disclosure. Other objects, advantages and novel features of the disclosure will be set forth in the following detailed description when considered in conjunction with the drawings.

DETAILED DESCRIPTION OF THE INVENTION

This disclosure pertains to a method to functionalize graphene to allow for modulation of graphene's electrical properties as well as for deposition of nanoparticles, such as oxides, metals, and quantum dots.

The effect of the non-covalent pyrene- and pyridine based functionalization on graphene's electromagnetic properties has not been explored in the prior art and is one of the purposes of this invention.

The covalent azide based functionalization was realized in a way that does not damage graphene (no D peak) and is thus unique to this work. As a result, we observed the quantum Hall effect in functionalized graphene that is typical only for pristine graphene systems. This discovery will help in the development of quantum Hall resistance standards based on graphene technology and provides a platform for other graphene devices such as sensors with superior electronic properties compared to other functionalization methods.

Both covalent and noncovalent chemical functionalization strategies for graphene were utilized.

Example 1

Figure 1:
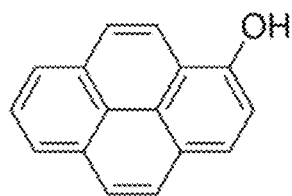
FIG. 1 illustrates schematics of pyrene-based and azide-based molecules used for epitaxial graphene functionalization. The pyrene-based molecules shown are 1-hydroxypyrene and 1 pyrenecarboxylic acid. The azide-based molecule shown is N-ethylamino-4-azidotetrafluorobenzoate (TFPA-$NH_2$).
Figure 1:
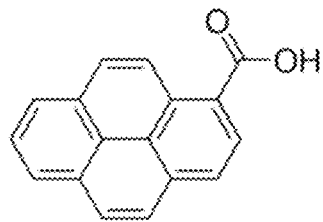
Figure 1:
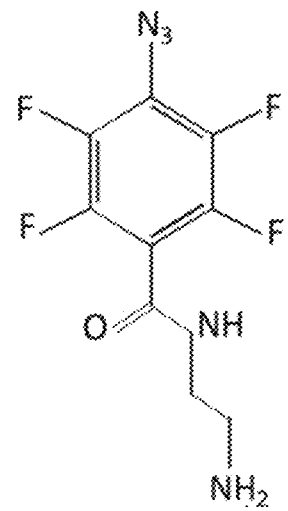

The non-covalent functionalization was based on π-π stacking between graphene and small-benzene ring containing molecules, as illustrated in FIG. 1.

Three molecules were used.

1-Hydroxypyrene solution was used as received.

The 1 pyrenecarboxylic acid was dissolved in methanol to make 20 mM solution. Graphene chips were incubated for 1 hour in both solutions.

In the case of 4-aminomethyl pyridine, the graphene chip was incubated at 190° C. for 6 hours.

Example 2

The covalent functionalization was based on the formation of a carbon bond between azide-containing molecules (FIG. 1) and graphene.

Two different molecules were used.

N-ethylamino-4-azidotetrafluorobenzoate (TFPA-$NH_2$).

Phosphorine-ethylamino-4-azidotetrafluorobenzoate (TFPA-$PO_3$).

4 ml solutions of both compounds were prepared in methanol. Then, the graphene chips were placed in solutions and exposed to UV light for 10-30 minutes.

Both functionalization types are tunable by adjusting solution molarity and incubation times. In the azide-based functionalization, the exposure time to UV is a critical parameter as well.

Example 3

After the functionalization, both covalent and non-covalent, was performed, the graphene chips were rinsed with methanol and isopropyl alcohol and dried with nitrogen.

Epitaxially grown graphene on SiC was used for the functionalization experiments. It should be noted that the functionalization strategies can be applied to CVD graphene as well.

Example 4

Epitaxial graphene was synthesized by means of Si sublimation from semi-insulating (SI), Si-face, on-axis, 6H-silicon carbide (SiC) substrates. The growth took place in a chemical vapor deposition reactor at a temperatures between 1540 and 1580° C. and a pressure of 100 mbar using Ar ambient. The argon was used to suppress the sublimation of Si in order to control the thickness of the epitaxial graphene layers.

Prior to growth, the substrates were in-situ $H_2$ etched to prepare the SiC surface for epitaxial graphene growth, by forming bilayer stepped morphology and removing any polishing scratches created during the manufacturing of the SiC substrate. Samples for the reference and functionalization with pyr-$NH_2$, pyr-OH and pyrene-OH were cooled in Ar to 800° C., at which point the reaction tube was evacuated.

The thickness of the epitaxial graphene layers was ~1.5 monolayers as measured by X-ray photoelectron spectroscopy.

The samples which were functionalized with TFPA-PO$_3$ and TFPA-NH$_2$ were cooled to 1050° C. in Ar after epitaxial growth, at which point the pressure was increased to 950 mbar and the Ar was replaced with H$_2$ to perform a hydrogen intercalation for 30 min. After the intercalation step, the sample was cooled in H$_2$ to 700° C. The hydrogen intercalation was used to make quasi-free standing graphene.

Example 5

Figure 2:
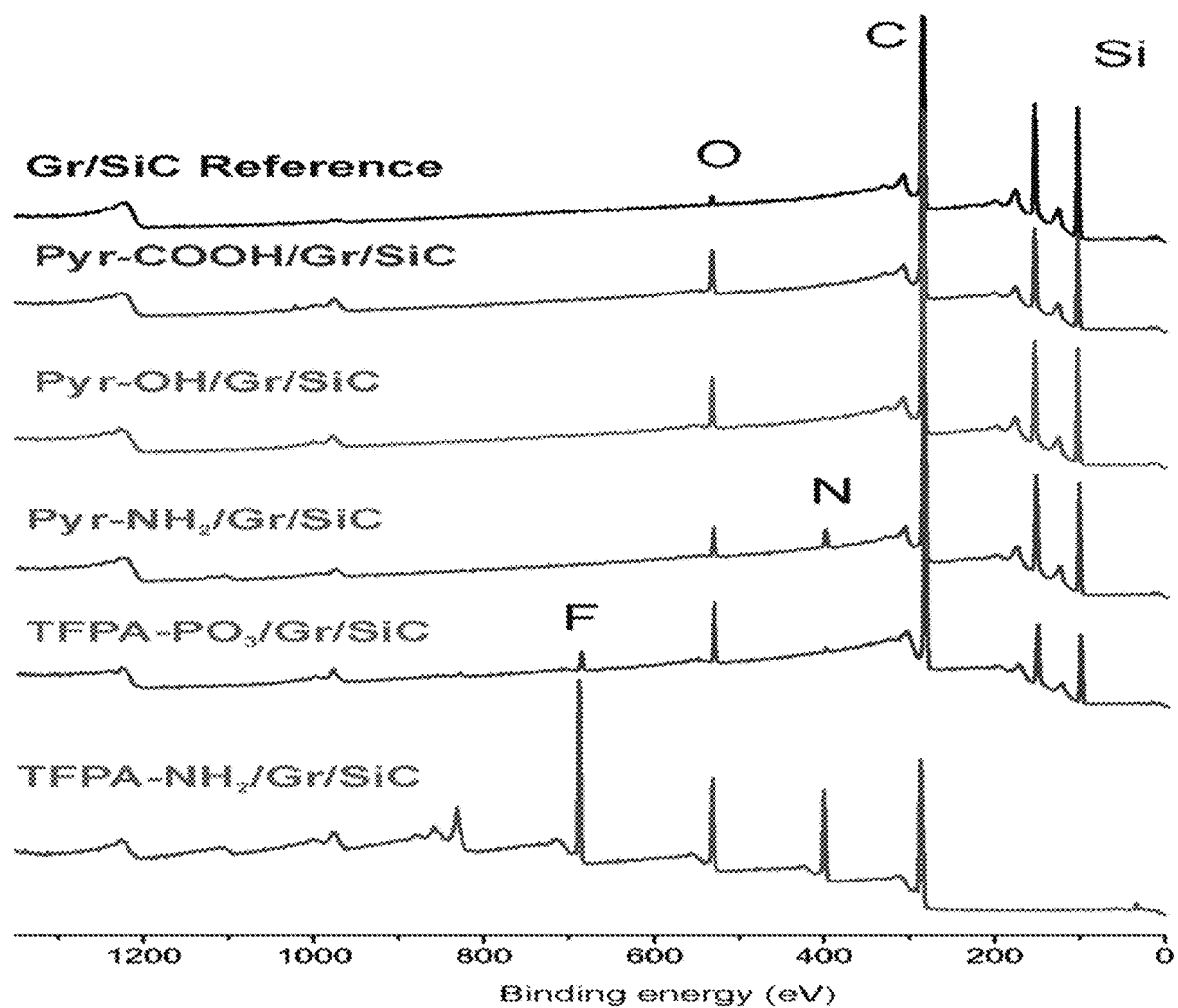
FIG. 2 illustrates XPS analysis of unfunctionalized and functionalized graphene.

The functionalization was confirmed by performing X-ray photoelectron spectroscopy analysis as shown in FIG. 2. Clearly, after functionalization with pyrene molecules containing OH— and COOH functional groups (1-hydroxypyrene and 1 pyrenecarboxylic acid) oxygen was detected 6.7 and 7.5 at. % respectively (FIG. 2, Table 1). Oxygen and nitrogen (4 at. %) were incorporated when the pyridine-NH$_2$ molecule was used. The covalent azide-based functionalization is characterized by incorporation of N and F in the case of NH$_2$-azide and O and F in the case of PO$_3$ azide.

TABLE 1

Chemical composition of pristine (reference) and functionalzied epitaxial graphene using chemical functionalization

|  | C1s | O1s | Si2p | N1s | F1s |
|---|---|---|---|---|---|
| Epi. Graphene Ref. | 65.23 | 1.33 | 33.44 |  |  |
| Graphene/Pyr-NH$_2$ | 64.59 | 4.17 | 27.51 | 3.73 |  |
| Graphene/Pyr-OH | 63.72 | 6.68 | 29.60 |  |  |
| Graphene/Pyr-COOH | 70.69 | 7.51 | 21.80 |  |  |
| Graphene/TFPA-PO$_3$ | 68.17 | 7.57 | 21.11 | 1.4 | 1.74 |
| Graphene/TFPA-NH$_2$ | 56.55 | 12.61 | 0 | 15.38 | 15.46 |

Example 6

Figure 3:
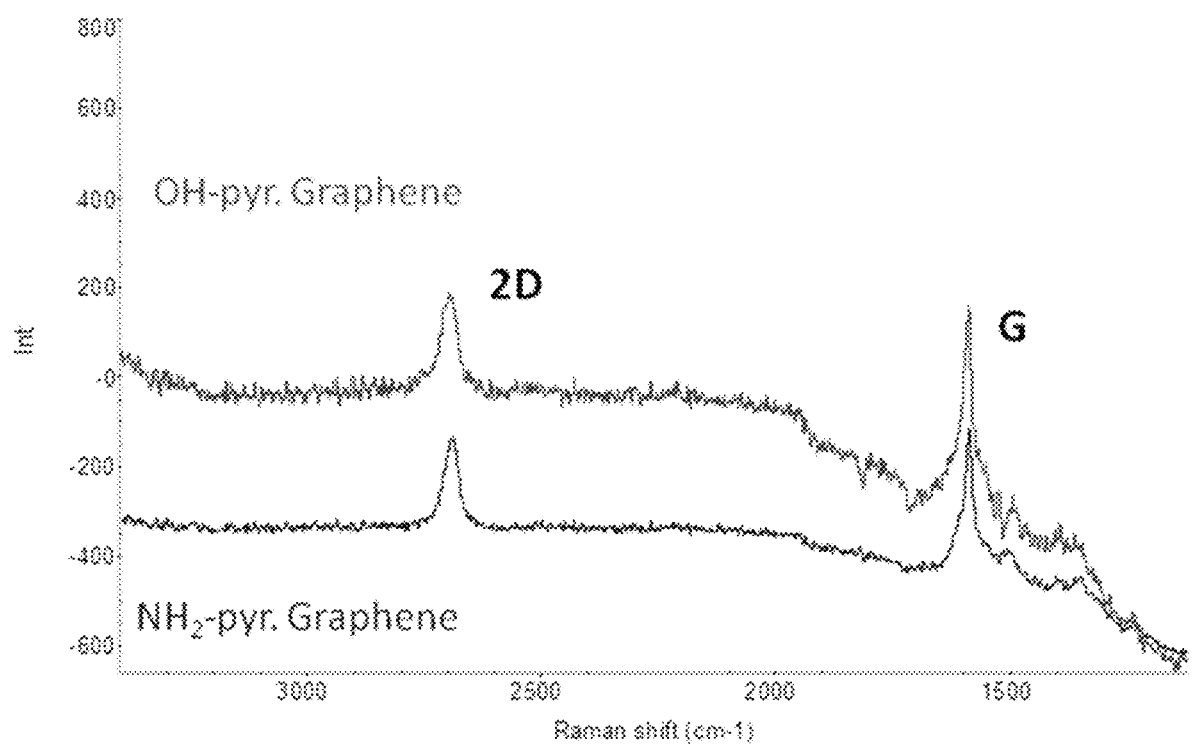
FIG. 3 illustrates Raman single point measurements pyrene-OH functionalized and pyridine-$NH_2$ functionalized epitaxial graphene. There is no indication of defect ($\sim 1350$ $cm^{-1}$) or induced strain in the graphene structure.
Figure 4:
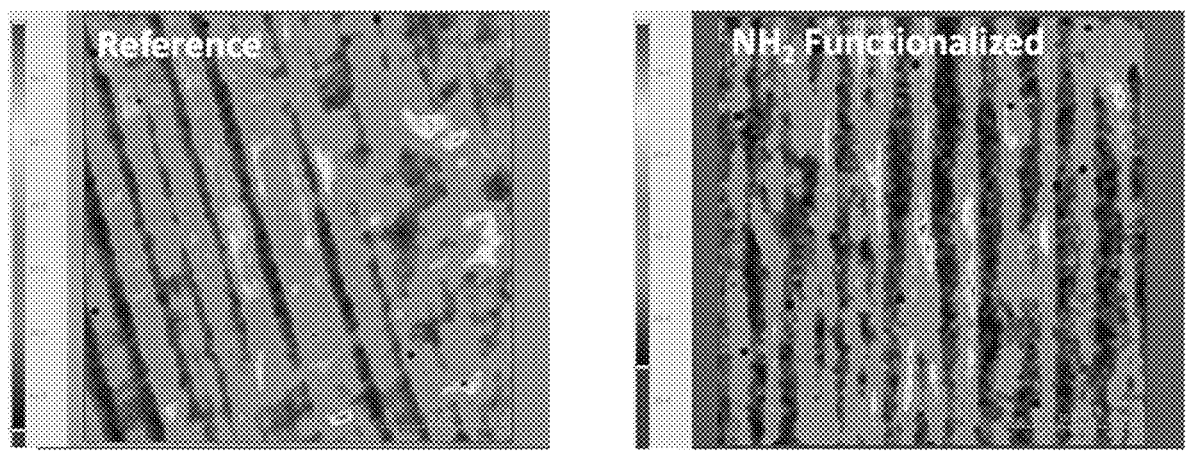
FIG. 4 illustrates 2D peak Micro-Raman maps of reference (untreated) epitaxial graphene on SiC and pyridine-$NH_2$ functionalized graphene. Step and terrace structure of the untreated graphene are replicated on the functionalized sample.

The effect of functionalization on graphene's structural properties was evaluated using Raman spectroscopy. Single point Raman analysis of OH-pyrene and pyridine-NH$_2$ functionalized graphene and micro-Raman maps are shown in FIGS. 3 and 4. While 2D and G peaks were clearly present, the D peak at 1350 cm$^{-1}$ was not (FIG. 3). The micro-Raman maps showed the preservation of epitaxial graphene terraces. There was no indication of defects or induced strain. Similar results were obtained for the other functionalization types (not shown).

Example 7

The electrical properties of pristine and functionalized graphene were characterized at room temperature using four-probe sheet resistance and Hall effect measurements as metrics. The results are summarized in Table 2. The pristine sample resistance was 1.44 kΩ/sq with the non-covalent functionalization increasing this value by a factor of approximately three. On the other hand, the covalent functionalization lowered the sheet resistance by a factor of approximately two.

To better evaluate the electrical characteristics of the samples, Hall measurements using the van der Pauw method with Cu clips to contact the four corners of the large area (8×8 mm) samples were performed. The graphene type, resistance, mobility and carrier concentrations are shown in Table 3.

The decreased sheet density implies that the functionalization results in compensatory p-doping, countering the natural n-doping of the sample. Consistent with the 4-probe measurements, the resistance, mobility and carrier concentration values of pristine and covalently functionalized graphene are similar. The values for the non-covalent functionalization also agree with the previous results, the functionalized graphene has reduced mobility, increased resistance and decreased carrier concentrations.

TABLE 2

Four probe sheet resistance measurements at room temperature over large scale.

|  | Attachment type | Resistance (kΩ/sq) |
|---|---|---|
| Epi. Graphene Ref. | None | 2.44 |
| Graphene/Pyr-NH$_2$ | Non-covalent | 5.9 |
| Graphene/Pyr-OH | Non-covalent | 7.25 |
| Graphene/Pyr-COOH | Non-covalent | 6.12 |
| Graphene/TFPA-PO$_3$ | Covalent | 0.72 |
| Graphene/TFPA-NH$_2$ | Covalent | 0.65 |

TABLE 3

Hall measurements of large area (8 × 8 mm) untreated (reference) and functionalized graphene/SiC substrates at room temperature using Cu clips measurements. The epi-graphene Ref. 1 refers to graphene grown epitaxially on Si-phase, i.e. (0001), of 6H-SiC. The epi-graphene Ref. 2 refers to graphene grown on Si-phase of SiC and then hydrogen intercalated.

|  | Type | Resistance Ωcm | Mobility cm$^2$/Vs | Sheet Conc. Cm$^{-2}$ |
|---|---|---|---|---|
| Epi-graphene Ref. 1 | p-type | 4.29 × 10$^{-5}$ | 947 | 1.53 × 10$^{13}$ |
| Epi-graphene Ref. 2 | p-type | 4.05 × 10$^{-5}$ | 739 | 2.08 × 10$^{13}$ |
| Graphene/Pyr-NH$_2$ | n-type | 3.4. × 10$^{-4}$ | 609 | −3 × 10$^{12}$ |
| Graphene/Pyr-OH | p-type | 5 × 10$^{-4}$ | 380 | 3.2 × 10$^{12}$ |
| Graphene/Pyr-COOH | n-type | 3.14 × 10$^{-4}$ | 485 | −4 × 10$^{12}$ |
| Graphene/TFPA-PO$_3$ | p-type | 5.41 × 10$^{-5}$ | 953 | 1.2 × 10$^{13}$ |
| Graphene/TFPA-NH$_2$ | p-type | 4.8 × 10$^{-5}$ | 952 | 1.37 × 10$^{13}$ |

Figure 5:
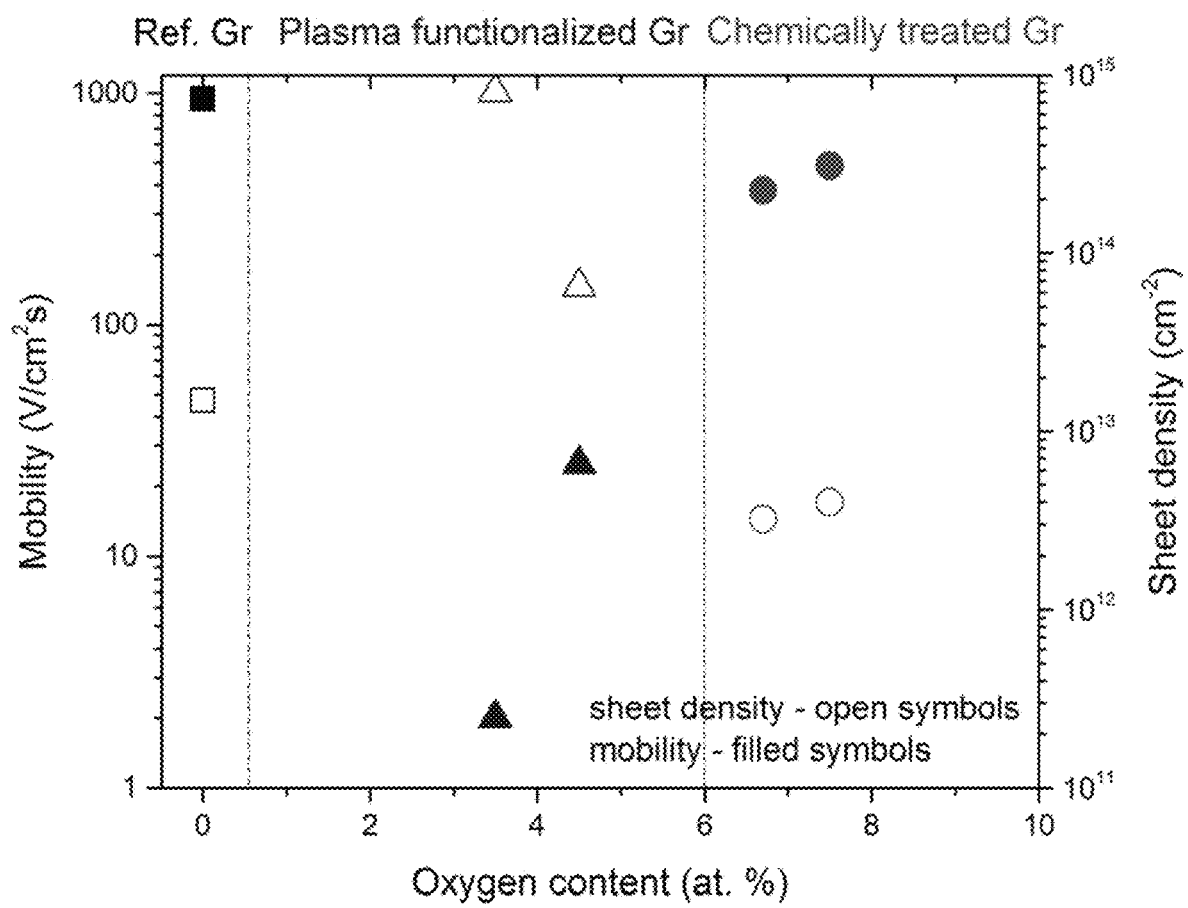
FIG. 5 illustrates a comparison between mobility and sheet density of plasma-based and chemical-based functionalized graphene measured using Hall effect measurement system of large area samples (8×8 mm) at room temperature.

A comparison between the mobility of oxygen plasma-based and chemical-pyrene based functionalization is shown in FIG. 5. These results were obtained using Hall-effect measurements of large area samples 8×8 mm at room temperature. As shown, while comparable functionalization levels were achieved, there is ∼ one order of magnitude improvement in mobility of the functionalized samples accompanied with an order of magnitude reduction in carrier density (20 vs. ∼ 400 cm$^2$/Vs, carrier density 6.5×10$^{13}$ vs. 3.2×10$^{12}$ cm$^{-2}$).

To understand this behavior temperature-dependent magnetotransport measurements of pristine and functionalized epitaxial graphene were performed. The temperatures were varied between 1.75 and 400 K in applied magnetic fields ±9 T using a Quantum Design Physical Properties Measurement System. To obtain accurate sheet resistance values, the square samples' four corners were wired in a Van der Pauw configuration by bonding 1-mil Au leads with Ag paint. The excitation currents used for these experiments were typically ∼ 1 μA DC.

Example 8

Figure 6:
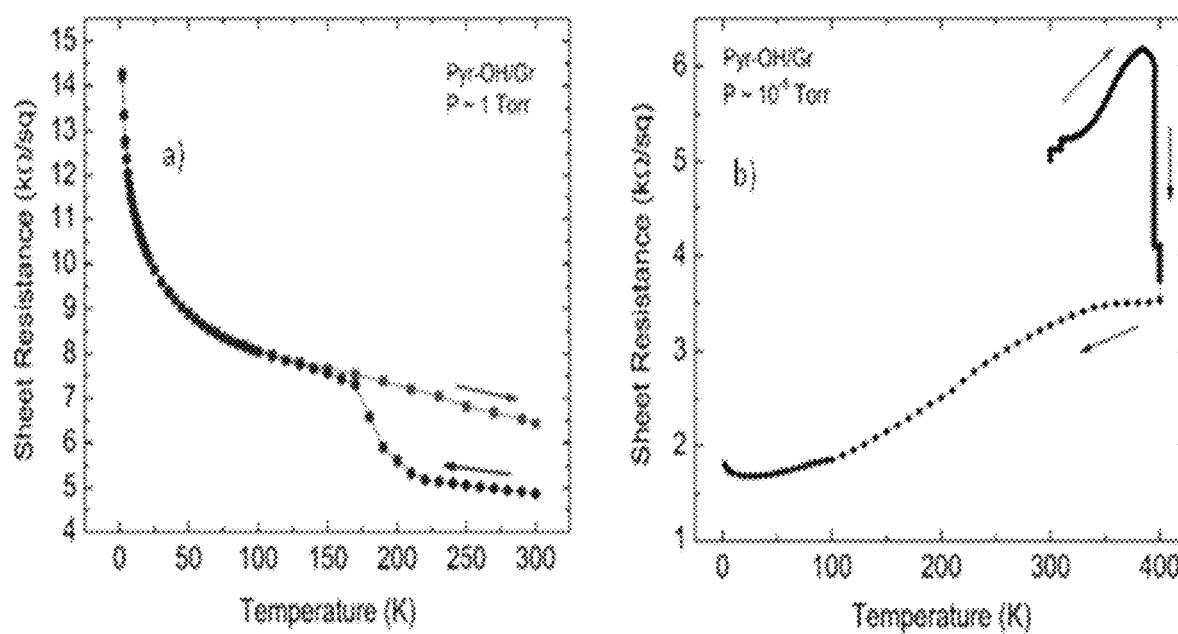
FIG. 6 illustrates heating and cooling of pyrene-OH functionalized samples for non-vacuum annealed sample and for in-situ vacuum annealed sample.

An irreversibility in the sheet resistance of functionalized samples was observed between runs of decreasing (T=300→1.75 K) and increasing (T=1.75→300 K) temperature that did not occur for pristine samples. This behavior was attributed to the enhanced sensitivity of functionalized graphene to gaseous adsorbates, such as those condensed on the sample's surface as the temperature is reduced. Thus, by in situ heating of the samples to 400 K in a high vacuum (P<$10^{-5}$ Torr) for several hours (FIG. 6), the adsorbates were released and intrinsic transport properties were recovered, enabling an accurate comparison of the various graphene functionalizations.

Example 9

Figure 7:
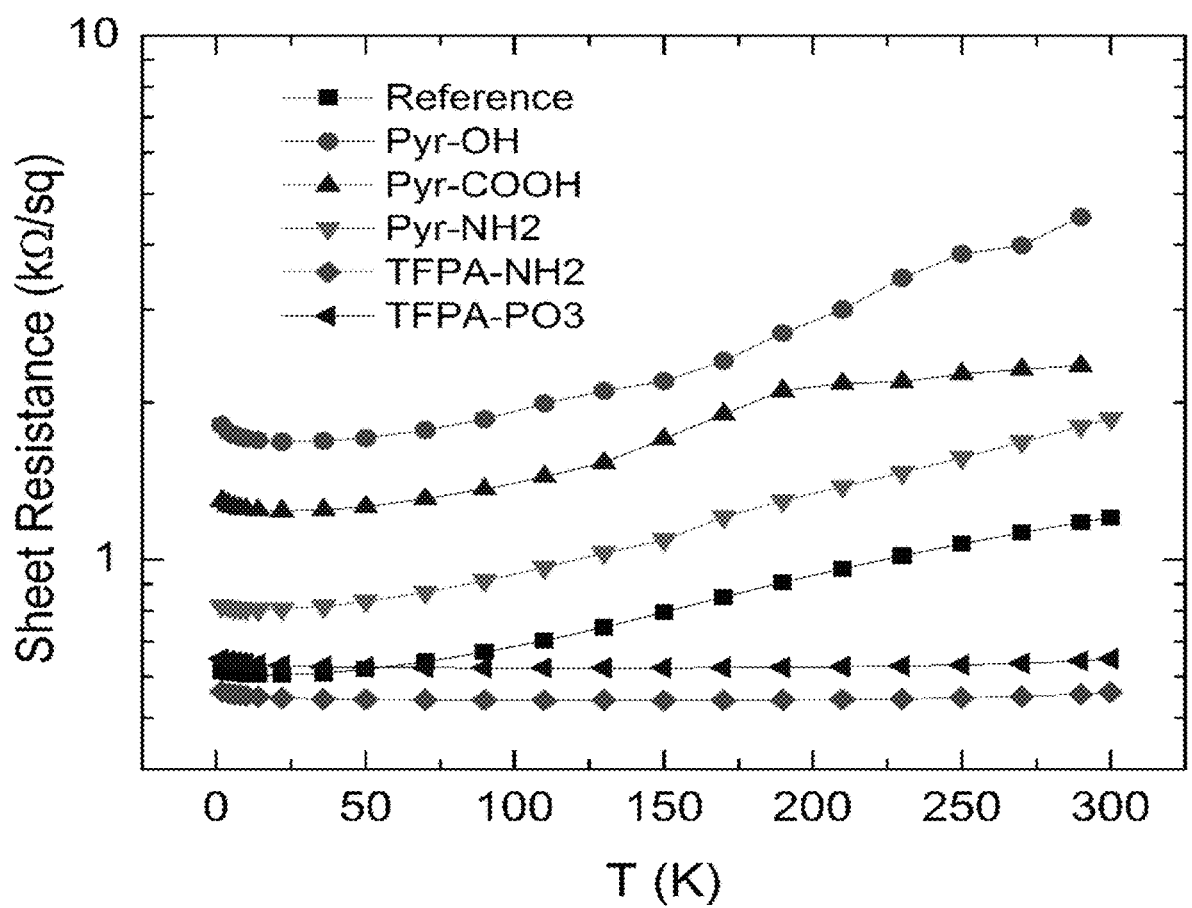
FIG. 7 illustrates sheet resistance variation as a function of temperature for pristine and chemically functionalized epitaxial graphene on SiC.

The sheet resistance variation as a function of temperature is shown in FIG. 7 on a semi-log plot for pristine and functionalized graphene.

Remarkably, the metallic transport of the reference sample is maintained after chemical functionalization.

At low temperature, the sheet resistance of TFPA functionalized and the pristine graphene samples was 600 Ω/sq, while for the pyrene-and pyridine once, the sheet resistance increased to 2 kΩ/sq.

By comparison, plasma functionalization of graphene causes increase in sheet resistance by an order of magnitude. In the case of nitrogen plasma functionalization (FIG. 8), the sheet resistance increased from 3 kΩ/sq to 600 kΩ/sq at low temperature.

These results suggest that the chemical functionalization allows for three orders of magnitude improvement of sheet resistance for the nitrogen functionalized samples (600 kΩ/sq vs 0.8 kΩ/sq for pyridine-$NH_2$).

Example 10

Figure 8:
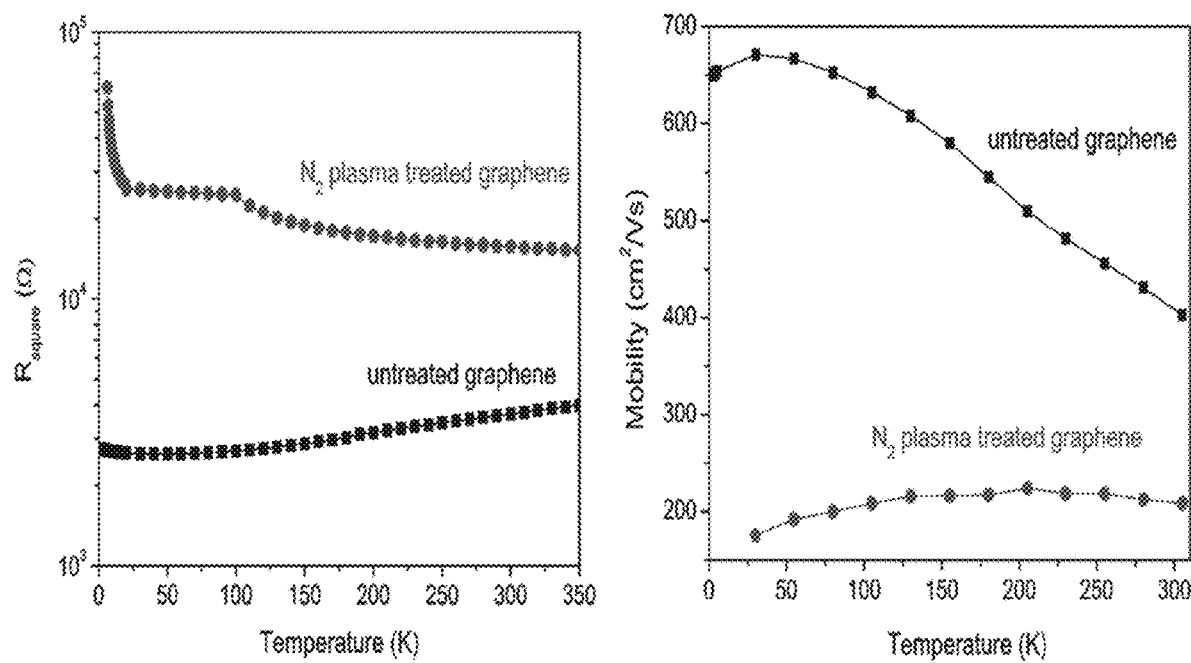
FIG. 8 illustrates sheet resistance and mobility variation as a function of temperature for pristine and nitrogen plasma functionalized epitaxial graphene on SiC.
Figure 9:
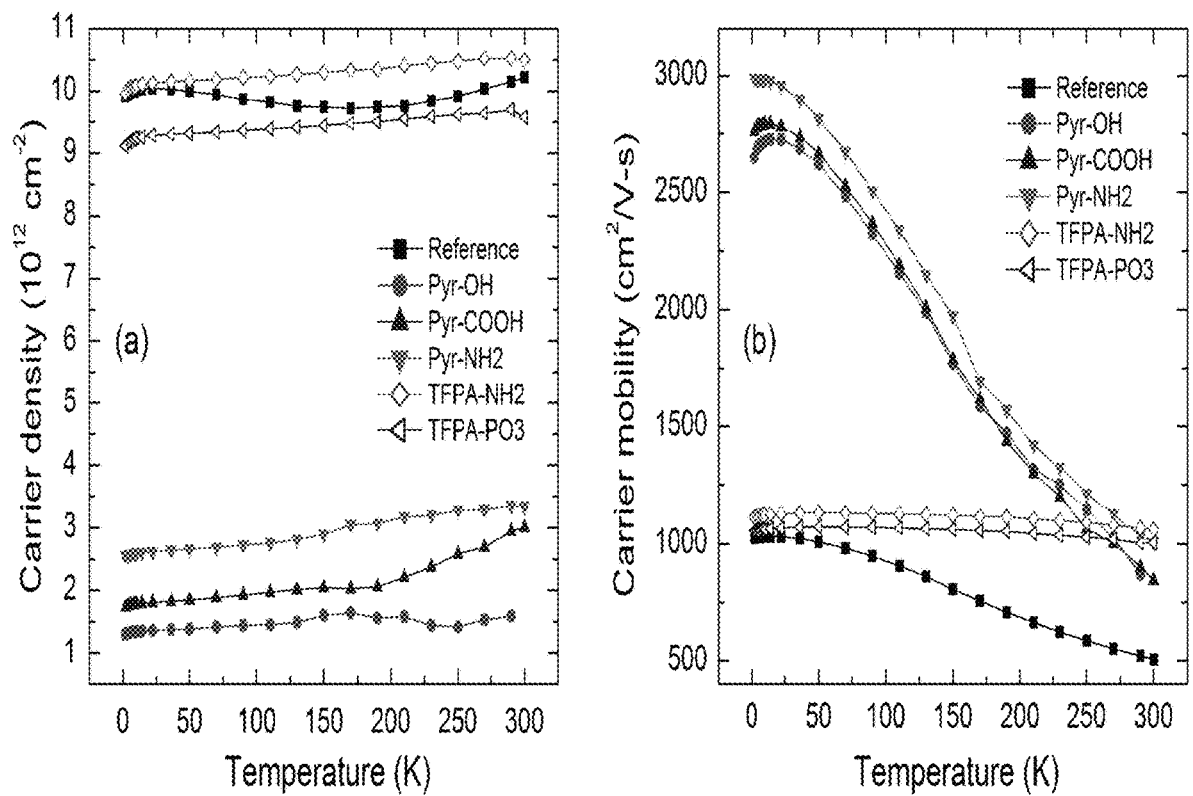
FIG. 9 illustrates carrier density (a) and mobility (b) of untreated (reference) and chemically functionalized graphene as a function of temperature. Closed (open) symbols correspond to electron (hole) charge carriers.

The mobility and charge-carrier density of chemically functionalized graphene as a function of temperature are shown in FIG. 9. The obtained results indicate that the pyrene and pyridine functionalization enhanced the transport properties of graphene, roughly tripling the mobility to 3000 $cm^2$/Vs at low temperatures while only slightly decreasing the carrier density. The azide-based functionalizations modestly improved the mobility of graphene as well. A comparable dose of plasma-functionalization induced disorder in the graphene, producing semiconducting-like transport and diminished electron mobility (FIG. 8).

In fact, the chemical pyrene-based functionalization closely mirrors an electric-field-gating induced shift of the Fermi level closer to the so-called charge neutrality point (CNP).

This is a key result since many functionalization methods result in greatly increased resistivity due to reduced mobility. The CNP is a characteristic of the 2D band-structure of graphene, which possess a linear dispersion above and below the Fermi level. In a conventional semiconductor, the electrons in the conduction band and the holes in the valence band are isolated by a band gap. However, in graphene, the tips of these bands come to a point, so that when the Fermi level is at this energy the carrier concentration for electrons and holes are equal. Thus, as one approaches the CNP due to the vanishing mass of the carriers that occurs in such systems.

Example 11

Figure 10:
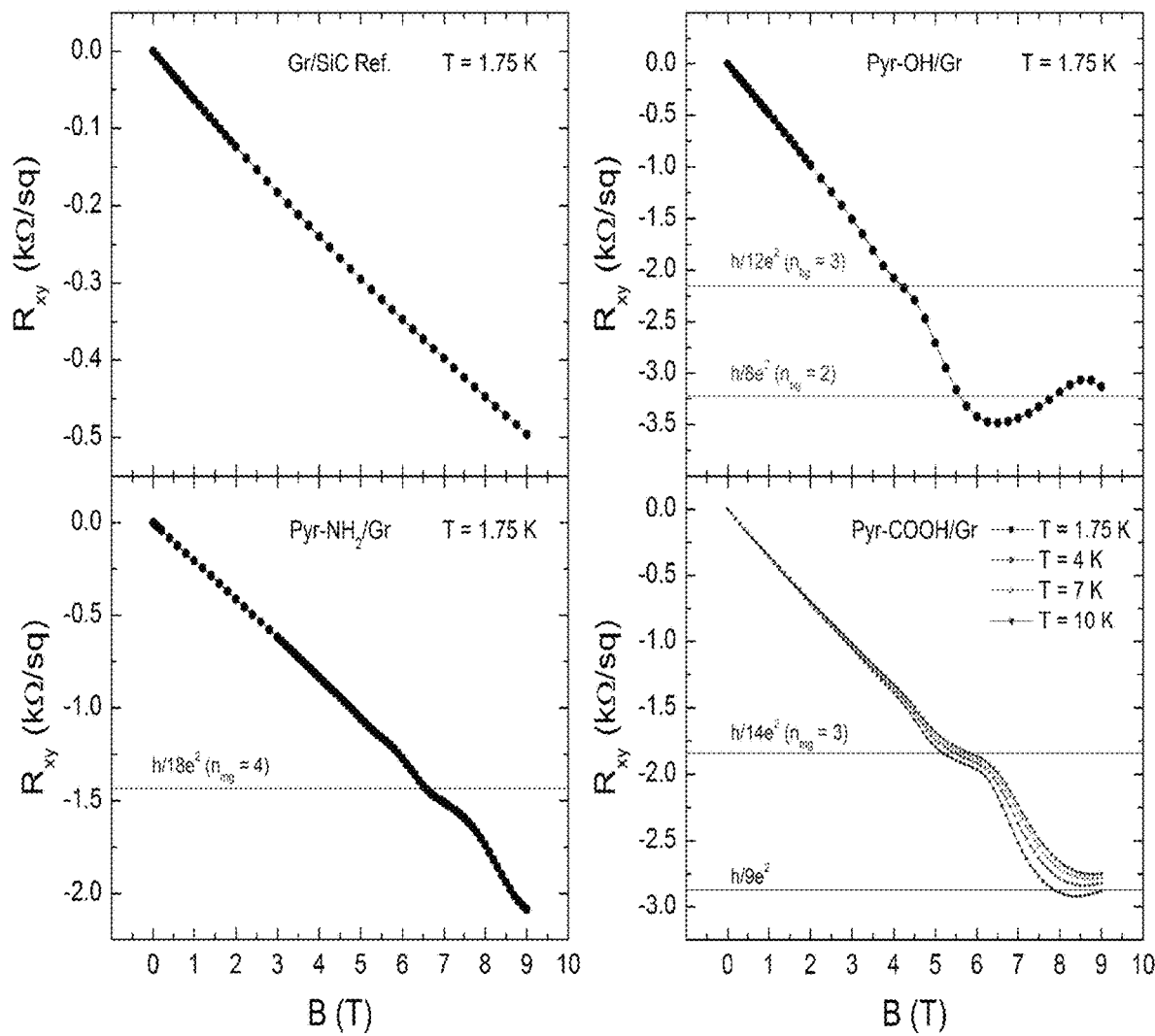
FIG. 10 illustrates Hall resistance versus magnetic field for pristine (reference) and chemically functionalized (pyrene- and pyridine-based) graphene. Horizontal lines and text indicate QHE plateau associated with monolayer (bilayer) graphene. The plateau at $R_{xy}=h/9e^2$ for Pyr-COOH/Gr could not be uniquely associated with monolayer or bilayer graphene, but may be a superposition of the two.
Figure 11:
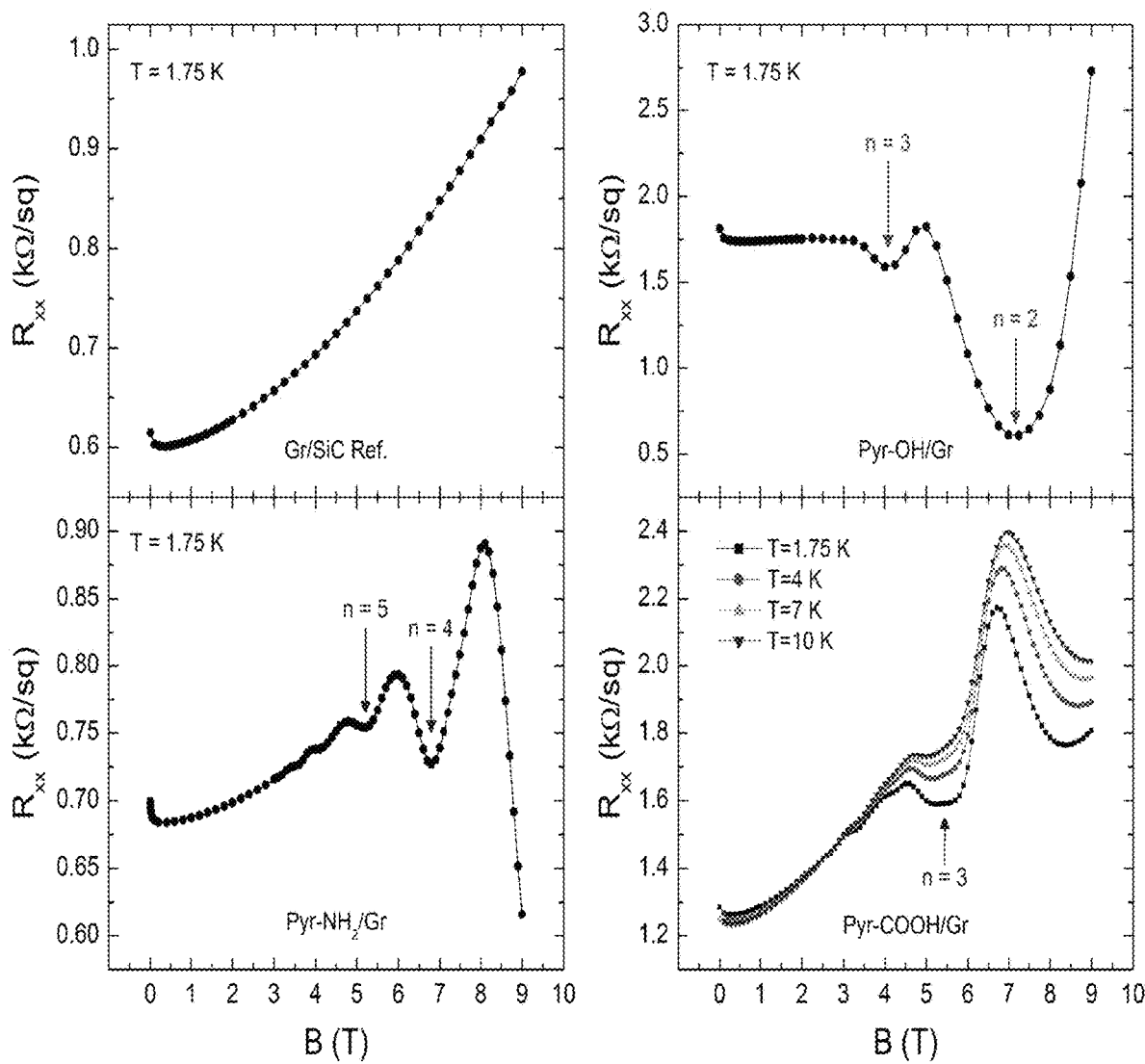
FIG. 11 illustrates longitudinal resistance versus magnetic field for pristine and pyridine-, pyrene-functionalized graphene. Shubnikov-de Haas oscillations on functionalized graphene.

To confirm that the mobility increase in our functionalized graphene is consistent with a shift of the Fermi energy ($E_F$) towards the CNP, we performed high magnetic field, low temperature Hall measurements, in an attempt to detect the quantum Hall effect (QHE). This phenomenon occurs exclusively in high mobility 2D electronic systems, and manifests as a series of plateaus in the field-response of the Hall resistivity ($R_{xy}$), and as local minima in the longitudinal magnetoresistance ($R_{xx}$); the latter are known as Shubnikov-de Haas oscillations (SDO). These features occur simultaneously as $R_{xy}$ reaches integer fractions of the quantum resistance (i.e. $R_{xy}=h/ie^2$, where i is an integer and h is Planck's constant). Monolayer and bilayer graphene can be distinguished by their respective, allowed values of i=4 ($n_{mg}+\frac{1}{2}$) and i=4$n_{bg}$, where $n_{mg}$=0, 1, 2, . . . and $n_{bg}$=1, 2, 3, . . . are their Landau Level (LL) indexes (a lower LL index means $E_F$ is to closer to the CNP). FIG. 10 displays $R_{xy}$ versus B for the pristine and the pyrene and pyridine functionalized graphene. While no identifiable plateaus appear in the reference sample, plateaus corresponding to monolayer and bilayer graphene LLs both appear in the functionalized samples. In addition, very clear SDO's are observed in the $R_{xx}$ versus B data in FIG. 11. Monolayer and bilayer graphene plateaus are detected because these unpatterned samples encompass many SiC terraces and steps, where monolayers and bilayers grow during synthesis, respectively.

Example 12

Figure 12:
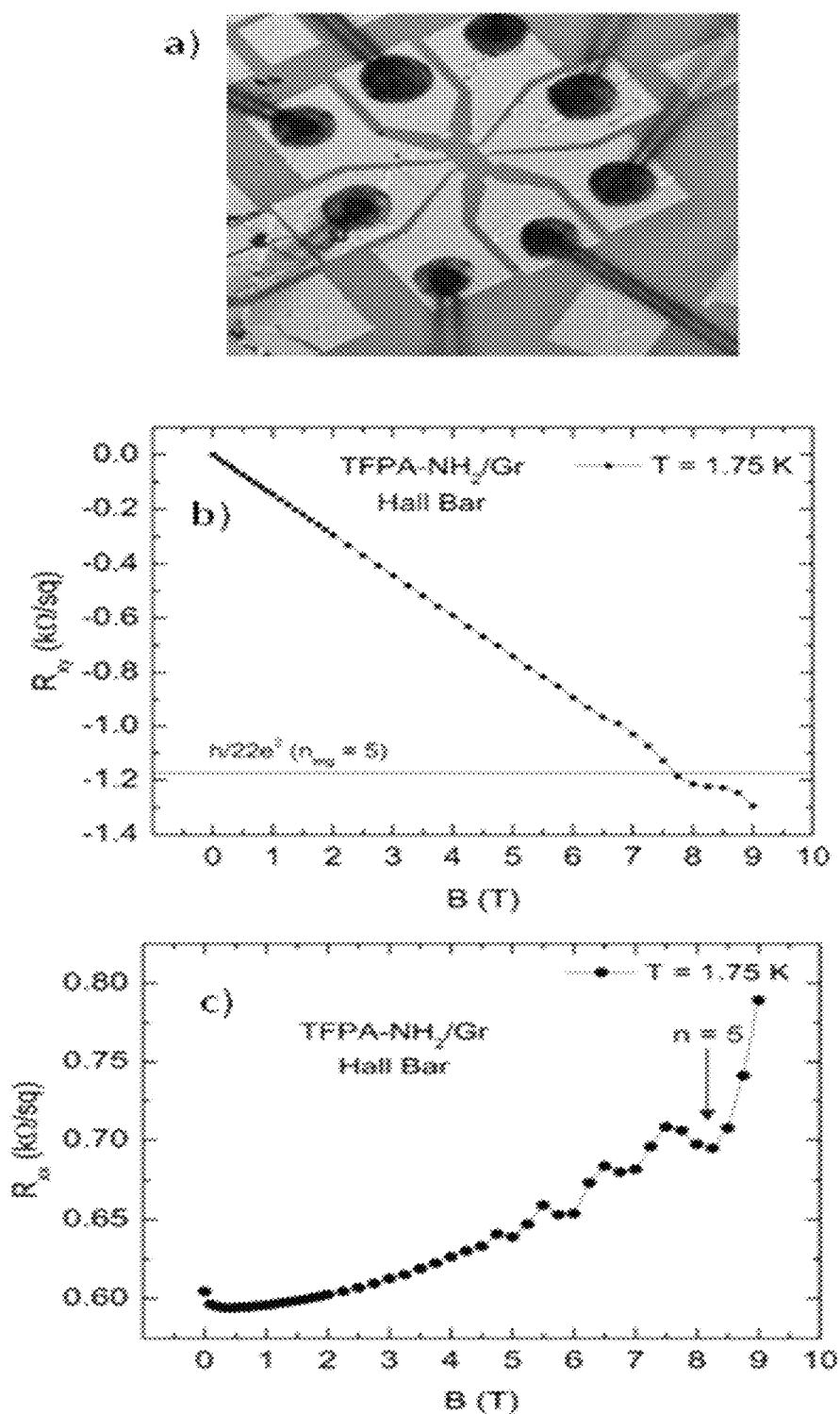
FIG. 12 illustrates Hall bar device onto TFPA-$NH_2$ functionalized graphene. Hall resistance and longitudinal resistance as a function of magnetic field for TFPA-$NH_2$ functionalized Hall-bar devices. Shubnikov-de Haas oscillations are present.
Figure 13:
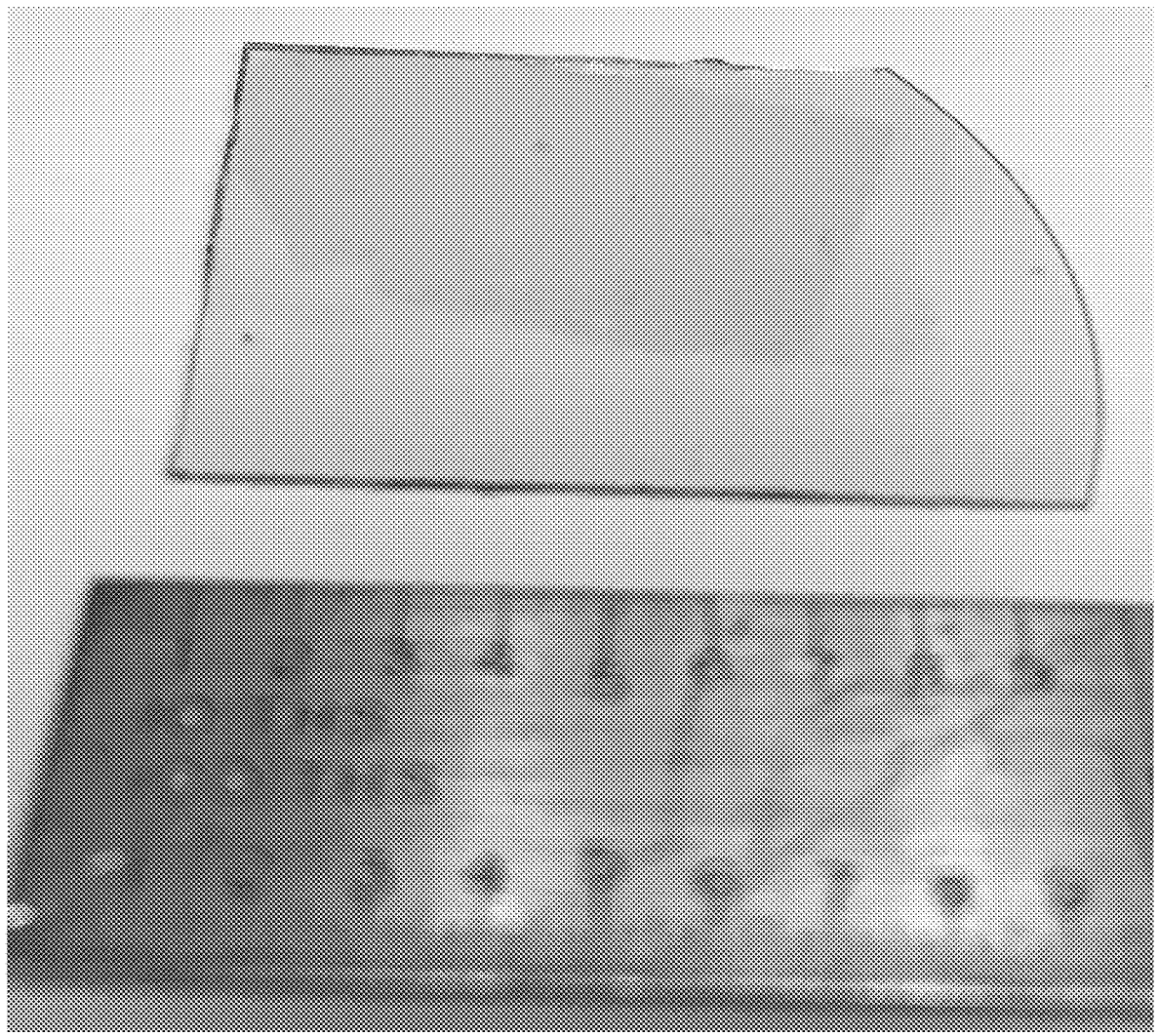
FIG. 13 illustrates sequential deposition of 2 L graphene onto functionalized single layer graphene.

Although the data for TFPA-functionalized graphene presented in FIG. 7 and FIG. 9 indicate a reduced sheet resistance and similar carrier density to the monolayer graphene reference, the functionalization was actually performed on hydrogen intercalated graphene, hence the p-type carrier mobility we observed. In addition, no QHE was observed in these samples. In order to accurately compare TFPA-based with pyrene and pyridine functionalization, we performed QHE measurements on a non-intercalated monolayer graphene sample that was patterned into a Hall bar over a single terrace and then functionalized with TFPA-$NH_2$, which is shown in FIG. 12. The QHE plateau in FIG. 12b and the SDO in FIG. 12 confirm that TFPA-$NH_2$ functionalization is indeed capable of promoting high-mobility quantum phenomenon in graphene.

If we assume that all samples are "dosed" equally and homogeneously, then the data would indicate that the Pyr-OH functionalization generates the best low temperature QHE attributes. This is based on the fact that a) the MR is relatively flat, with large SdH oscillations that dominate the field response, and b) the QHE plateau (which has some longitudinal component leaked in because of the VdP geometry) is more pronounced at lower fields and occurs at the N=2 Landau level, though it is the LL for a bilayer graphene. These results are consistent with the data in FIG. 9, which shows a maximal reduction in the carrier concentration compared to the reference, indicative of a shift of $E_F$ closer to the Dirac point, along with a large enhancement in mobility. Overall, the TFPA-functionalizations exhibit weaker QHEs versus Pyr-functionalizations. Of the Pyr-functionalizations, the worst would be the Pyr-NH2, because the LL indexes are higher in value (4 and 5) for the same fields that produced N=2 in the others.

Functionalization of graphene allows for: attachment of sequential graphene layers, attachment of other two dimensional materials including boron nitride, $MoS_2$, phosphorene; and attachment of nanoparticles to the graphene surface such as oxides, metals, and quantum dots.

The proof of principle experiment was conducted by placing $HNO_3$ bottom functionalized graphene floating in H$_2$O to TFPA-NH$_2$ functionalized single layer graphene/Al$_2$O$_3$. The sheet resistance of the top layer was 275 Ohm/sq.

Nanoparticle deposition to graphene is important for increase of selectivity and sensitivity of graphene chemical sensors. Even though the method shown below is for attachment of ZnO nanoparticles, this approach can be used to attach any oxide nanoparticles to graphene i.g. TiO$_2$, FeO$_2$, CuO etc. The method can be further expanded to other nanoparticles e.g. gold nanoparticles by simply changing the linker molecule end group from amine (NH$_2$) to thiol (SH).

Example 13

Figure 14:
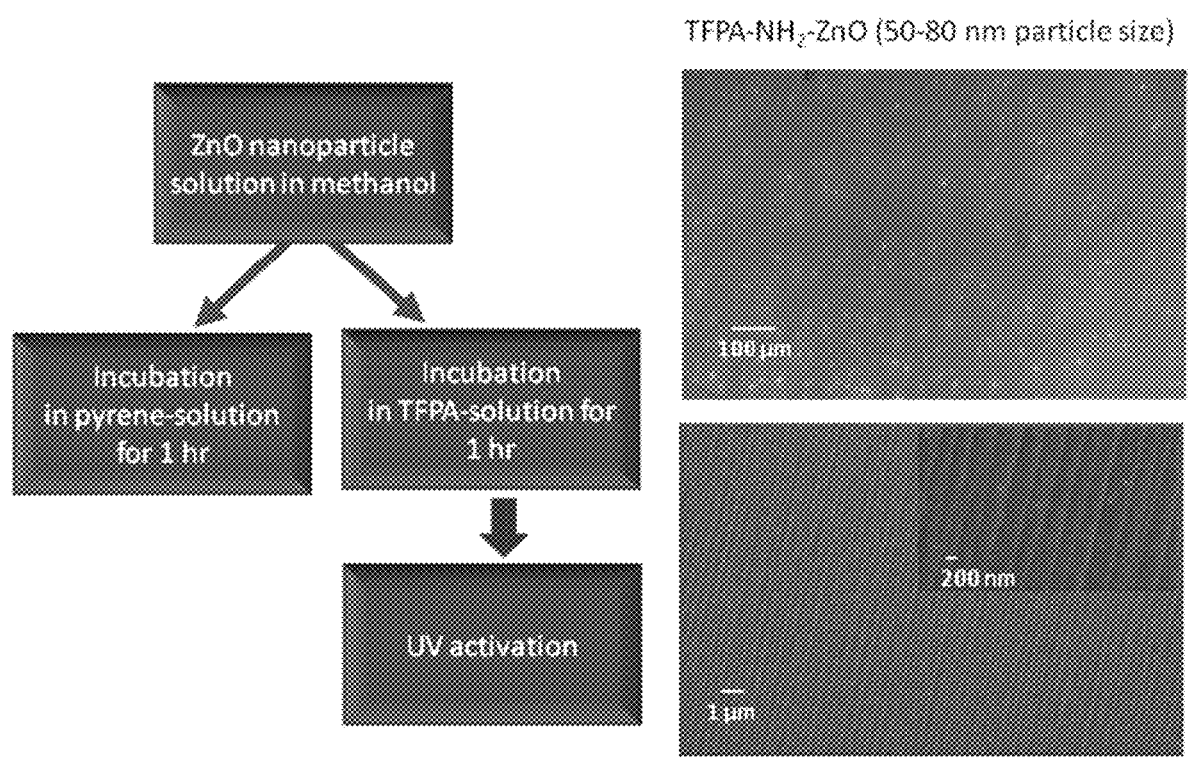
FIG. 14 illustrates functionalization of graphene with ZnO nanoparticles. SEM images of TFPA-$NH_2$—ZnO functionalized epitaxial graphene.

ZnO nanoparticles in suspension in water were purchased from US Nanoresearch materials. The experiments were performed using 50-80 nm particles as 20 wt. % dispersion in water. Multiple dispersions of ZnO nanoparticles in methanol were prepared (Table 4). The starting dispersion was a (1:20) dilution of the purchased dispersion and labeled "dispersion 1". This dispersion was further diluted and pyrene-COOH and TFPA-NH$_2$ were added (FIG. 14). The particles were then incubated for 1 hour at room temperature. After that epitaxial graphene/SiC was placed in the solutions and the dispersion was exposed to a 460 W Hg UV lamp (Oriel instruments) for 20 minutes. The samples were then rinsed with methanol and iso-propanol. The ZnO attachment was verified by X-ray photoelectron spectroscopy. A higher Zn signal was detected when the pyrene-solution was used. However, the SEM images of the azide-based functionalization showed better coverage.

TABLE 4

Dispersions of ZnO nanoparticles

| | ZnO dispersion volume (ml) | MeOH volume (ml) | Compound (gr) |
|---|---|---|---|
| Dispersion 1 | 1 ml | 20 ml | |
| Dispersion 2 | 100 ul from solution 1 | 20 ml | 0.022 gr pyr-COOH |
| Dispersion 3 | 1 ml solution 1 | 20 ml MeOH | 0.025 gr TFPA-NH$_2$ |
| Dispersion 4 | 1 ml solution 2 | 10 ml MeOH | |
| Dispersion 5 | 1 ml solution 3 | 10 ml MeOH | |

Example 14

Pyrene-based molecules with SH-functional group or TFPA-SH can be used to attach gold nanoparticles or quantum dots to graphene. The TFPA-SH has the same structure as the main molecule (TFPA-NH$_2$ but has the NH$_2$ (amine) functional group substituted with SH (thiol) functional group). Gold nanoparticles or quantum dots attached to graphene will allow for different optoelectronics applications of graphene.

Example 15

NHS-based pyrene molecule or synthesizing TFPA-NHS molecule can be used to attach a large range of biomolecules to graphene including peptides, proteins, DNA, or antibodies, thus allowing the functionalized graphene to be used in biosensing applications.

Example 16

TFPA-NH$_2$ molecule can be used to functionalize boron nitride on Cu foil and we successfully achieved a large degree of functionalization. Boron nitride (BN) is another two-dimensional material and is typically recognized as the best substrate for graphene—the highest graphene electron mobilities have been measured when graphene sits on BN. Typically BN/graphene heterostructures are from van der Waals type, meaning, that there is no attachment between the two materials. Note that in their natural state graphite (from which graphene was isolated) and boron nitride are lubricants, so nothing sticks to them. In the literature, there are only a few studies (3-4 papers) discussing functionalization of boron nitride powder. We have functionalized boron nitride film on Cu foil.

Therefore, our covalent functionalization of graphene (TFPA-NH$_2$) can be extended to other 2D-materials. The group through which the attachment happens is the azide group (N$_3$) similar to graphene, thus allowing boron nitride functionalization with a whole series of TFPA molecules (TFPA-PO$_3$, TFPA-SH, TFPA-OH, TFPA-NHS) that allows attachment of gold nanoparticles, metal oxide nanoparticles, biomolecules etc.

Example 17

Metal dicalcogenides (TMDs) such as MoS$_2$, MoSe, WS$_2$, and WSe can also be attached to graphene and boron nitride. This attachment is accomplished by using TFPA-SH or pyrene-based molecule with SH functional group incorporated into its structure. In this case, the SH (thiol) functional group will attach to the TMDs and the N$_3$ (azide) functional group will attach to the graphene and to the boron nitride.

There are many advantages and new features with the current invention.

For example, a high degree of functionalization was achieved without deterioration of graphene's electrical properties (over three orders of magnitude improvement of sheet resistance at low temperatures over the state of the art for plasma functionalization).

Also, the synthesis of high mobility functionalized samples (3000 cm$^2$/Vs at low temperature) represents a p-doping effect that compensates the natural n-type doping known to be present in ML graphene.

The compensatory p-doping effect of the current invention can be used to control uniformity of carrier density and mobility over a quantum Hall device thus paving the way of graphene resistance standard.

Our functionalization approach enables a covalent one step attachment of ZnO nanoparticles to graphene which could subsequently be used in a sensor. By extension, the functionalization approach can enable the attachment of a wide range of nanoparticles or chemical molecules compatible with functional group.

Additionally, our functionalization approach can be used to create a scaffolding so that the deposition of thin dielectric films on epitaxial graphene can be accomplished without impacting the electronic properties of the graphene; subsequent device structures could be used in a wide range of applications such as RF field effect transistors, mixers, and future device functionalities.

Furthermore, this approach can be applied to chemical functionalization of graphene oxide with chemical moieties and then thermal reduction to graphene. It should be noted that this type of "functionalized graphene" is appropriate for biosensing and energy applications. However, for electronics device applications single layer of graphene is better compared to reduced graphene oxide due to its far superior electronics properties.

The above examples are merely illustrative of several possible embodiments of various aspects of the present disclosure, wherein equivalent alterations and/or modifications will occur to others skilled in the art upon reading and understanding this specification and the annexed drawings. In addition, although a particular feature of the disclosure may have been illustrated and/or described with respect to only one of several implementations, such feature may be combined with one or more other features of the other implementations as may be desired and advantageous for any given or particular application. Also, to the extent that the terms "including", "includes", "having", "has", "with", or variants thereof are used in the detailed description and/or in the claims, such terms are intended to be inclusive in a manner similar to the term "comprising".

What we claim is:

1. A method for graphene functionalization and nanoparticles deposition, comprising:
   providing graphene;
   functionalizing the graphene via non-covalent functionalization wherein the step of functionalizing the graphene via non-covalent functionalization comprises the steps of
      providing one from the group consisting of 1-hydroxypyrene solution, 1 pyrenecarboxylic acid dissolved in methanol, and 4-aminomethyl pyridine; and
      incubating the graphene;
   attaching a sequential graphene layer onto the functionalized graphene;
   rinsing the graphene;
   drying the graphene; and
   forming functionalized graphene wherein the functionalized graphene preserves electronic properties; and
   depositing nanoparticles on the functionalized graphene, wherein the nanoparticles comprise oxide nanoparticles.

2. The method for graphene functionalization and nanoparticles deposition of claim 1 further comprising the steps of dissolving the 1 pyrenecarboxylic acid in methanol and making a 20 mM solution.

3. The method for graphene functionalization and nanoparticles deposition of claim 1 wherein the step of incubating the graphene is for 1 hour if using 1-hydroxypyrene solution or 1 pyrenecarboxylic acid.

4. The method for graphene functionalization and nanoparticles deposition of claim 1 wherein the step of incubating the graphene is for 6 hours at 190° C. if using 4-aminomethyl pyridine.

5. The method for graphene functionalization and nanoparticles deposition of claim 3 wherein the step of rinsing the graphene uses methanol and isopropyl alcohol and wherein the step of drying the graphene uses nitrogen.

6. The method for graphene functionalization and nanoparticles deposition of claim 1 further comprising the steps of:
   utilizing a nanoparticle suspension in water;
   mixing the nanoparticle suspension in water with methanol and forming a working solution;
   incubating the working solution in pyrene-solution or TFPA-solution and thereby attaching the nanoparticle to the graphene;
   applying UV to the nanoparticle and the graphene;
   activating the nanoparticle attachment to the graphene; and
   rinsing and drying the graphene comprising the attached nanoparticle.

7. The method for graphene functionalization and nanoparticles deposition of claim 6 wherein the step of applying UV to the nanoparticle and the graphene is for about 10-30 minutes.

8. A method for graphene functionalization and nanoparticles deposition, comprising:
   providing graphene;
   functionalizing the graphene via non-covalent functionalization wherein the step of functionalizing the graphene via non-covalent functionalization comprises the steps of
      providing one from the group consisting of 1-hydroxypyrene solution, 1 pyrenecarboxylic acid dissolved in methanol, and 4-aminomethyl pyridine; and
      incubating the graphene;
   attaching a two dimensional material onto the functionalized graphene, wherein the two dimensional material is one selected from the group consisting of $MoS_2$ and phosphorene;
   rinsing the graphene;
   drying the graphene; and
   forming functionalized graphene wherein the functionalized graphene preserves electronic properties; and
   depositing nanoparticles on the functionalized graphene, wherein the nanoparticles comprise oxide nanoparticles.

9. A method for graphene functionalization and nanoparticles deposition, comprising:
   providing graphene;
   functionalizing the graphene via covalent functionalization wherein the step of functionalizing the graphene via covalent functionalization comprises the steps of
      providing one from the group consisting of N-ethylamino-4-azidotetrafluorobenzoate (TFPA-$NH_2$) in methanol, TFPA-OH, TFPA-COOH, TFPA-SH, TFPA-NHS, and phosporine-ethylamino-4-azidotetrafluorobenzoate (TFPA-$PO_3$) in an organic solvent selected from the group consisting of methanol, toluene, and dichloromethane; and
      incubating the graphene;
   rinsing the graphene;
   drying the graphene; and
   forming functionalized graphene wherein the functionalized graphene preserves electronic properties; and
   depositing nanoparticles on the functionalized graphene, wherein the nanoparticles comprise oxide nanoparticles.

10. The method for graphene functionalization and nanoparticles deposition of claim 9 further comprising the step of:
   attaching a sequential graphene layer onto the functionalized graphene.

11. The method for graphene functionalization and nanoparticles deposition of claim 9 further comprising the step of:
   attaching a two dimensional material onto the functionalized graphene, wherein the two dimensional material is one selected from the group consisting of boron nitride, $MoS_2$, and phosphorene.

12. The method for graphene functionalization and nanoparticles deposition of claim 9 further comprising the steps of:
   utilizing a nanoparticle suspension in water;
   mixing the nanoparticle suspension in water with methanol and forming a working solution;

incubating the working solution in pyrene-solution or TFPA-solution and thereby attaching the nanoparticle to the graphene;
applying UV to the nanoparticle and the graphene;
activating the nanoparticle attachment to the graphene; and
rinsing and drying the graphene comprising the attached nanoparticle.

\* \* \* \* \*